United States Patent [19]

Wendler

[11] Patent Number: 5,554,141
[45] Date of Patent: Sep. 10, 1996

[54] THERMOPLASTIC URIDOM AND METHOD AND APPARATUS FOR THE MANUFACTURING THEREOF

[75] Inventor: Henrik G. Wendler, Frederiksberg, Denmark

[73] Assignee: Colplast A/S, Denmark

[21] Appl. No.: 191,757

[22] Filed: Feb. 4, 1994

Related U.S. Application Data

[63] Continuation of Ser. No. 719,779, filed as PCT/DK91/00129, May 14, 1991, abandoned.

[30] Foreign Application Priority Data

May 15, 1990 [DK] Denmark .................................. 1201/90

[51] Int. Cl.$^6$ ..................................................... A61F 5/44
[52] U.S. Cl. .......................................... 604/352; 604/349
[58] Field of Search ................................. 604/349–352; 128/842, 844

[56] References Cited

U.S. PATENT DOCUMENTS

| | | | |
|---|---|---|---|
| Re. 33,206 | 5/1990 | Conway et al. .................. | 604/349 |
| 3,339,551 | 9/1967 | Stoutenburgh .................. | 604/349 |
| 3,520,305 | 7/1970 | Davis ............................... | 604/349 |
| 3,721,243 | 3/1973 | Hesterman et al. ............. | 604/353 |
| 3,835,857 | 9/1974 | Rogers, III et al. ............. | 604/349 |
| 4,062,361 | 12/1977 | Poulsen . | |
| 4,378,018 | 3/1983 | Alexander et al. . | |
| 4,551,490 | 11/1985 | Doyle et al. . | |
| 4,626,250 | 12/1986 | Schneider ........................ | 604/353 |
| 4,784,655 | 11/1988 | Campion et al. ................ | 604/349 |
| 4,806,091 | 2/1989 | Linns et al. . | |
| 4,806,092 | 2/1989 | Linns et al. . | |
| 4,806,093 | 2/1989 | Linns et al. . | |
| 4,808,105 | 2/1989 | Linns et al. . | |
| 4,808,174 | 2/1989 | Sorkin . | |
| 4,817,593 | 4/1989 | Taller et al. . | |
| 4,840,625 | 6/1989 | Bell .................................. | 604/349 |
| 4,885,049 | 10/1989 | Johannesson ................... | 604/349 |
| 4,892,903 | 1/1990 | Himes ............................. | 525/89 |
| 4,955,392 | 9/1990 | Sorkin ............................. | 128/844 |
| 5,059,190 | 10/1991 | Novak ............................ | 128/844 |
| 5,089,550 | 2/1992 | Sakagami et al. .............. | 525/314 |

FOREIGN PATENT DOCUMENTS

| | | |
|---|---|---|
| 305270 | 7/1970 | Denmark . |
| 137243 | 2/1978 | Denmark . |
| 791549 | 7/1979 | Denmark . |
| 842292 | 5/1984 | Denmark . |
| 843113 | 6/1984 | Denmark . |

(List continued on next page.)

OTHER PUBLICATIONS

Technical Bulletin Shell Chemical Company, *KRATON Polymers, G 2730X, G 273X, D 2120X and D 2121X for Elastomeric Films*, May 1989.

Primary Examiner—Randall L. Green
Assistant Examiner—Robert Clarke
Attorney, Agent, or Firm—Ostrolenk, Faber, Gerb & Soffen L.L.P

[57] ABSTRACT

A uridom for use as an external male catheter in a urinary incontinence device is manufactured by thermoplastic processing, using as base material a non-preprocessed compound material based on one or more thermoplastic, polystyrene-based block copolymers, preferably polystyrene polyethylene/butylene polystyrene copolymers, the elasticity of which has been enhanced through addition of a paraffinic process oil.

In the thermoplastic processing a constricted tubular portion at one end of the device is produced by injection moulding in a tool, serving as drainage tube and connected to a tube, whereas a mainly cylindrical, thin-walled body portion (1) is produced integral with said tube portion by a subsequent controlled extrusion and blow moulding operation, during which operation the said tube portion is secured and retained in said tool, whereby not only said tube portion but also an adjacent end portion of the body portion are produced with controlled increased wall thickness as compared with the rest of the body portion.

13 Claims, 7 Drawing Sheets

FOREIGN PATENT DOCUMENTS

| | | |
|---|---|---|
| 150792 | 1/1988 | Denmark . |
| 0177254 | 9/1986 | European Pat. Off. . |
| 0390720 | 3/1990 | European Pat. Off. . |
| 3822743 | 1/1989 | Germany . |
| 3220791 | 1/1989 | Germany . |
| 2168283 | 6/1986 | United Kingdom . |
| 8911258 | 11/1989 | WIPO . |

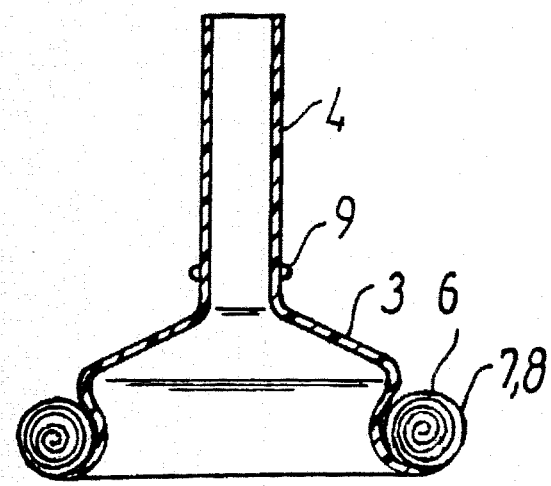
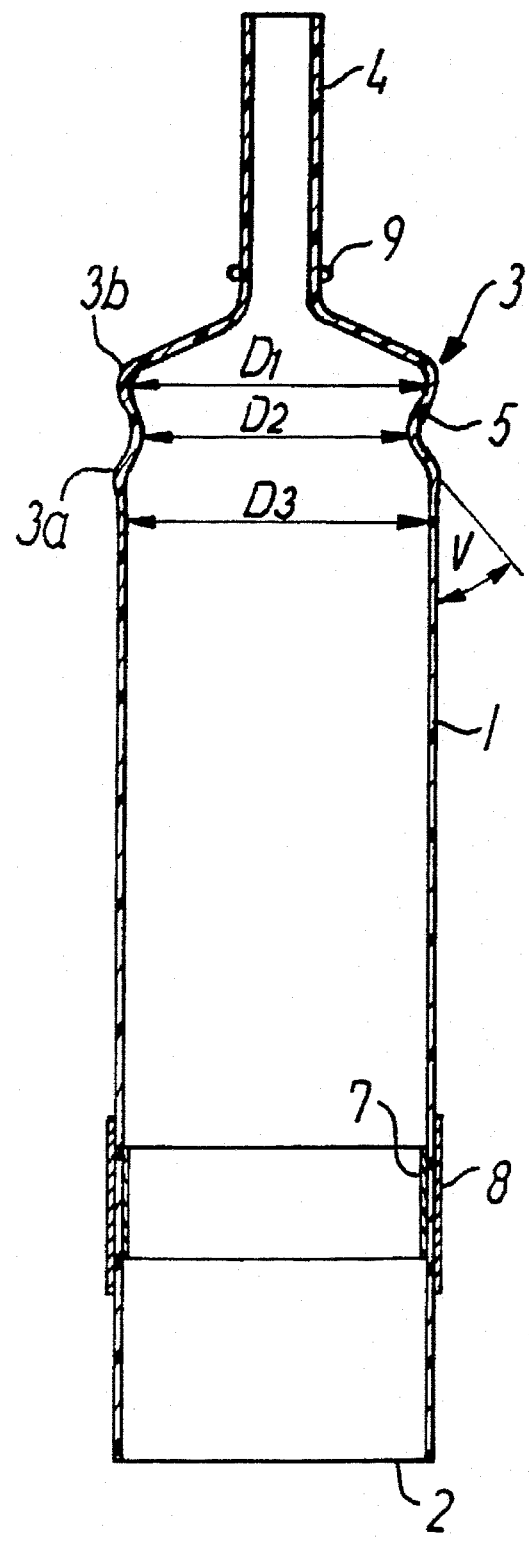

THERMOPLASTIC URIDOM AND METHOD AND APPARATUS FOR THE MANUFACTURING THEREOF

This is a continuation of application Ser. No. 07,719,779 filed on Jun. 24, 1991 now abandoned, which is a continuation-in-part of International Application No. PCT/DK91/00129, filed May 14, 1991.

BACKGROUND OF THE INVENTION

1. Field of the Invention

The invention relates to a uridom for use as an external catheter in a male urinary incontinence device, manufactured by thermoplastic processing of a non-preprocessed thermoplastic elastomeric base material.

2. Description of the Related Art

For aiding male urinary incontinence and for use in hospitals in connection with treatment and surgery of urethral disorders a urinary incontinence device is normally used, consisting of a uridom designed to be arranged as an external catheter on the penis and having a comparably short tube which via a hose is connected to a urine collection bag that is normally fastened to the user's leg.

Uridoms for use in such incontinence devices are produced in a conventional way like other elastic tubular sheaths to be fastened on parts of the human body, i.e. of natural latex by a multi-step dipping process, during which a mandrel of the same size and shape as the part of the body concerned is dipped repeatedly into a latex solution, which in between immersions is cured on the mandrel.

This known method which, i.a. is disclosed in the European Publication No.0 390720 suffers from several deficiencies in practice.

The latex used is thus a natural product, which may vary in respect of quality and composition and may i.a. contain allergy-inducing proteins, which in an industrial production is an impediment to ensuring a constant product uniformity with an optimum skin comfort. This is further intensified by the fact that the latex solution contains a vulcanization system, which among other substances contains nitrosamines and sulphur.

Furthermore, the lifetime of latex products is shortened by the fact that their structure contains double linkings which are sensitive when exposed to UV radiation, resulting in a decomposition of the material, whereby the properties of the product may deteriorate drastically.

In addition, this production method leaves much to be desired from an environmental and manufacturing point of view. In the process ammonia is employed and often also methanol and inorganic salts, wherefore a continuous destruction of chemical residues that are detrimental to the environment must take place. A possible waste resulting from a faulty production or excess material cannot be recycled but must be discarded and destroyed.

Also, the latex dipping method is a relatively lengthy process with a typical production lead time in the range of 24 hours, meaning that industrial mass production requires comprehensive machinery.

To alleviate or avoid these disadvantages a number of propositions have been made relating to the production of uridoms and similar products using different materials and methods.

The Danish patent application No.1549/79 thus discloses a method for manufacturing prophylactic devices such as condoms and fingerstalls by thermomoulding, whereby an extruded piece of a film of a thermoplastic polyurethane elastomer is deformed by means of a mandrel. The method thus requires a preprocessing of the PUR material into film and a subsequent extrusion into small units which in the moulding process are heated to a temperature high enough to soften the material.

Applying this method it is difficult to obtain the thin wall thickness, 150–200 u, which is required of a uridom and, added to this, polyurethane does not have sufficiently good elastic properties to be a user-friendly alternative to the conventional latex uridoms, inasmuch as a polyurethane product will be perceived as tight.

In addition, base materials which are based on polyurethanes contain substances that are detrimental to the environment, such as, e.g. isocyanate.

U.S. Pat. No. 4,817,593 discloses a method for manufacturing condoms by which a mandrel is dipped into a polyurethane solution in an organic solution and is cured at a high temperature. Contrary to the latex technology the mandrel is dipped into the solution only once, but the method does not remedy the above-mentioned deficiencies in using polyurethane as base material.

U.S. Pat. No. 4,808,174 discloses a method for manufacturing condoms of plastics such as polyethylene, polypropylene or vinyl. The method is identical to the one described in the above-mentioned Danish patent application, i.e. preprecessed films are heated to a temperature which is high enough to soften them and are then moulded on a mandrel.

The Danish publication No.137 243 describes a method for manufacturing rubber products by repeated dipping into an elastomer solution consisting of a SBS or SIS block copolymer strained with 5–100 percentage by weight of a mainly naphtenic/aromatic petroleum oil and dissolved in 200/1200 percentage by weight of an aliphatic hydrocarbon, preferably petrol. The method first and foremost implies an environmental hazard, because comparably large quantities of solvents are employed and, furthermore, the thermoplastic block copolymers of the type described do not sufficiently remedy the problems of deterioration and wear which are found in latex products. It has also been found that in uridoms manufactured by applying this method, a comparatively high decontraction occurs which may be due to a too low softening temperature, and which entails that a rolled-up uridom is difficult to unroll after only a few weeks of storage.

In the Danish publication No.150 792 a method for manufacturing uridoms is proposed, according to which an extruded hose-like body of thermoplastic and elastic material is blown up in a mould. As possible materials to be used for the extrusion of the tubular body are mentioned granulated latex, rubber or thermoplastic raw material. The method has never been put into practice and the description does not give any guidelines for solving the specific product-related and environmental problems mentioned above- The publication must be considered as a rather theoretical proposition for a production method as an alternative to the known latex dipping process without providing adequate documentation for its industrial applicability.

The published international patent application WO 89/11258 discloses a contraceptive condom made of thermoplastic material and manufactured by blow extrusion or blow moulding, where a tubular film body is either extruded by an embedded air bubble or heated and put in a mould and blown up by means of compressed air. Subsequently, one end portion of the tubular body is automatically sealed closed.

For functional reasons it is desirable that the part of the tube which serves as drainage tube should have a certain rigidity with a view to its being connected to a tube connector and, in order to achieve an anti-kinking function, it is preferred that in an adjacent end portion of the otherwise thin-walled body portion a constriction should be provided to serve as an anti-kinking chamber.

The above-mentioned European patent application No.0390720 describes the manufacture of such a uridom by a conventional latex dripping process.

SUMMARY OF THE INVENTION

Against this background it is the object of the invention to provide a uridom having said properties, whereby not only the observed deficiencies and disadvantages inherent in latex products are eliminated, but also the unfortunate properties and unwarranted side effects of the alternative solutions described above.

According to the invention a uridom is characterized in that a tubular portion at one end of the uridom, serving as drain for connection to a tube is produced by injection moulding in a tool, whereas a mainly cylindrical and thin-walled body portion is produced integral with said tubular portion by a subsequent controlled pull extrusion and blow moulding process, during which said tubular portion, which has increased wall thickness, is secured and retained in said tool.

As compared with latex, a synthetic and well-defined material has been used as base material, which can be produced without any content of allergy-inducing substances or other substances that make the finished products less gentle to the skin. It has proved feasible to produce a uridom which has sufficient elasticity, so that the finished product relatively easily can be deformed and thereby is not perceived as tight, which also entails that a rolled-up uridom even after having been stored for a considerable length of time can be unrolled without major difficulty.

As the production method consists in a purely thermo-plastic processing of a non-preprocessed base material, the disadvantages related to the processing which are inherent in the known dipping methods are avoided, whether in these are employed latex solutions or other solutions such as possibly thermoplastic elastomers. The production method according to the invention represents a cleaner technology, insofar as no chemical residues are generated that may be detrimental to the environment and which have to be destroyed, and all waste or excess material from the production can be recycled, as it is generally known from the processing of thermoplastic materials.

Financially, this production method has the advantage that thermoplastic processing is of a short duration with a very short production lead time, as the process in principle merely comprises heating, moulding and cooling.

According to the invention, in addition to these process-related advantages a significantly enhanced freedom of choice in respect of product design is obtained, due to the combination of injection moulding and extrusion/blow moulding, among other things as concerns variations of the wall thickness in the longitudinal direction of the products.

A preferred embodiment is thus characterized in that one or more zones in the longitudinal direction of the body portion have an increased wall thickness as compared with the otherwise thin-walled body portion.

The invention also relates to a method for manufacturing the uridom, which method is characterized in that the said tubular portion is produced by injection moulding, during which process a thermoplastic base material is fed in a plastic state through a stationary first mould part to a pouring cavity in an adjacent movable second mould part, and that after the injection moulding, by a pull extrusion operation, during which the said second mould part is moved away from the stationary first mould part, a hose-like member is produced which is integral with the said tube portion during continued feeding of the base material, and that the portion is produced by blow moulding of said portion in a cavity, the side walls of which are formed by mould wall parts introduced between said first and second mould part, and that the rate of speed in the movement of said second mould part away from the stationary first mould part during the pull extrusion operation is controlled to impart to the hose-like member a controlled increase of the wall thickness in one or more zones in the longitudinal direction of the body portion.

According to the invention, for production of uridoms, as said non-preprocessed compound materials are preferably employed one or more polystyrene polyethylene/butylene polystyrene block polymers, the elasticity of which has been increased by adding a paraffinic process oil. A particularly well suited base material can be obtained on the basis of the compound materials marketed by Shell Chemical Company under the trade name "KRATON-G-Polymers".

With a view to the injection moulding process forming part of the production method a slight amount of a release agent is preferably added to the base material.

The elasticity enhancing addition of said paraffinic oil will preferably be in the range of 60–85 parts of said process oil per 100 parts of the above-mentioned preferred compound material, whereby precisely the above-mentioned advantageous combination of material properties is obtained.

For use in manufacturing the uridom when applying the method described above an apparatus is devised which is characterized in that a stationary first mould part is formed with a mainly cone shell-shaped feeding duct for said base material in plastic state with a annular nozzle orifice in a side wall of said mould part, that a second injection mould part is arranged for movement towards and away from said side wall of the stationary mould part, and having a cylindrical pouring cavity which at one end is open towards the side wall of said mould part, designed for positioning against the annular nozzle orifice, control means being provided for moving the injection mould part away from the first mould part with securing and retaining of said tube portion during an trusion operation, two blow mould parts being designed and positioned for introduction between the first mould part and the injection mould part for provision of mould walls for a blow moulding process.

BRIEF DESCRIPTION OF THE DRAWINGS

The invention will be further explained in the following with reference to the schematical drawing, in which FIG. 1 shows a sectional view of a preferred embodiment of a uridom according to the invention in rolled-up form;

FIG. 2 shows a sectional view of a preferred embodiment of a uridom according to the invention in an unrolled form;

DETAILED DESCRIPTION OF THE PREFERRED EMBODIMENTS

Figure 3:
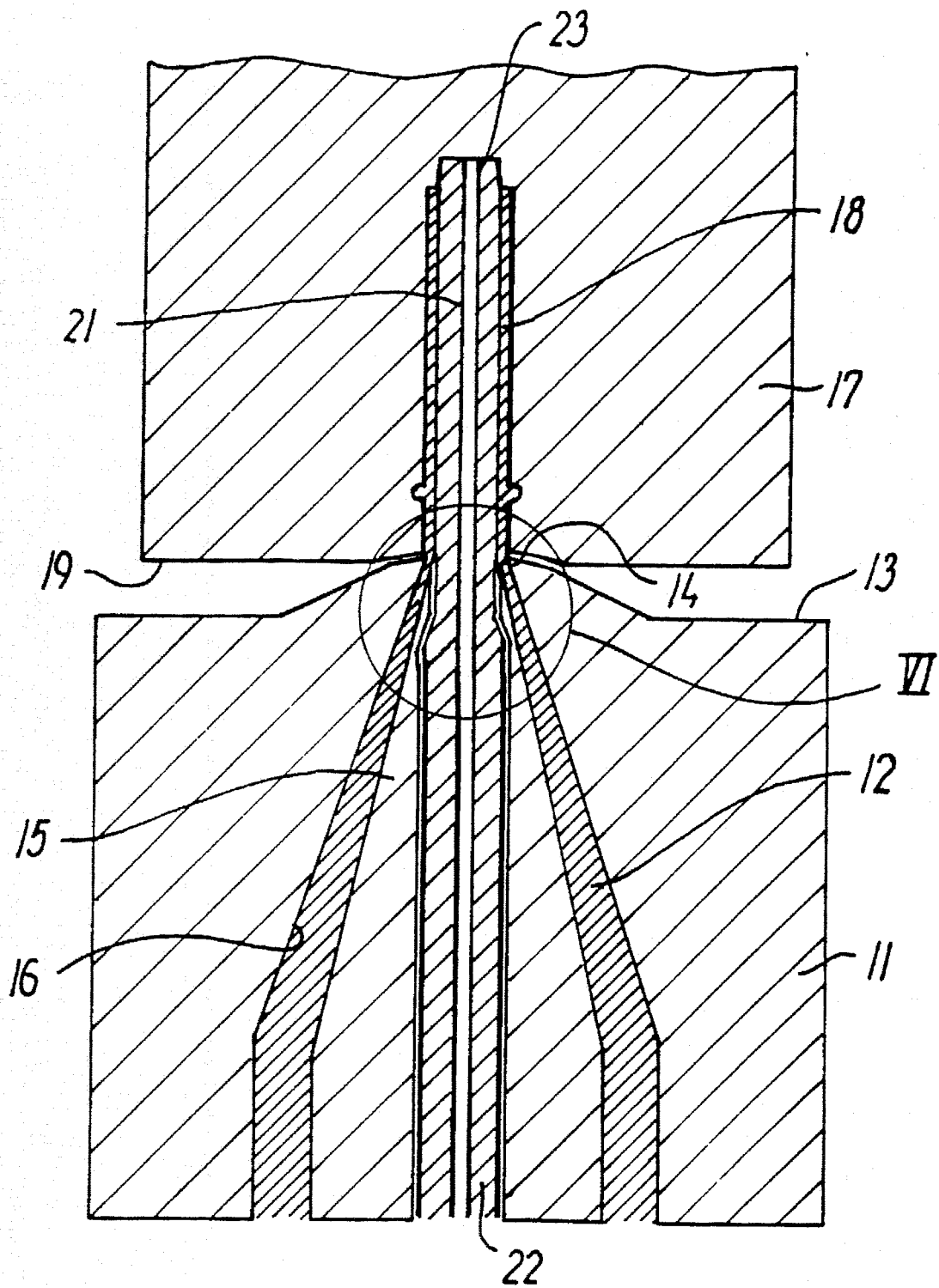
FIG. 3 illustrates the manufacture of the uridom through an injection moulding process.

The uridom shown in FIGS. 1 and 2 comprises a soft thin-walled and flexible body portion 1 with an open end 2. At the opposite end the body portion 1 contracts towards an end portion 3 having increased wall thickness and rigidity as compared with the body portion 1.

The end portion 3 comprises a first portion 3a with a maximum interior diameter $D_3$ corresponding to the interior diameter of the body portion 1 and a second portion 3b, which is integral with a narrow discharge or drainage tube 4, which by means of a tube can be connected to a not shown urine collection bag, which normally is fastened to one of the user's legs.

Between the first and second portion 3a and 3b of the end portion 1, a constriction 5 is provided, having such axial and radial dimensions, that the body portion 1 in the rolled-up supply condition shown in FIG. 1 can be received and retained in the constriction. The second portion 3b of end portion 3 between the constriction 5 and the drainage tube 4 converges towards the drainage tube 4 from a maximum diameter $D_1$, which is larger than the bottom diameter $D_2$ of the constriction 5 in order to provide an anti-kinking chamber, which according to the prior art prevents kinking of the drainage tube 4 and thereby back-flow of urine during use of the uridom.

As shown in FIG. 2, part of the inner side of the body portion 1, as it is known per se from the International Patent Application WO86/00816, can be provided with an integral layer 7 of a pressuresensitive adhesive, and on the outer side with a matching adhesive-rejecting layer 8 in order to prevent successive windings in the rolled-up body portion 6 from sticking together.

Furthermore, with a view to the production method described in the following, the uridom is provided, in the illustrated preferred embodiment, with a circumferential bead 9 around the drainage tube.

As distinct from the conventional uridom designs as shown in FIGS. 1 and 2, where the uridom is made of latex and produced by repeated dipping and during operations as, e.g. disclosed in the abovementioned U.S. Patent Publication, the uridom according to the invention is produced by a method which solely involves thermoplastic processing of a base material in the form of a non-preprocessed compound material based on one or more thermoplastic, polystyrene-based block copolymers, the elasticity of which has been enhanced by adding a paraffinic process oil, which causes increased elasticity and which at the same time results in less force being required to unroll a rolled-up uridom.

As main component of the compound material are preferably used one or more polystyrene polyethylene/burylens polystyrene copolymers, preferably those marketed by Shell Chemical Company under the trade name "KRATON"-G-Polymers.

Tests have shown that especially a combination of the specific polymers designated KRATON-G-1650 and KRATON-G-1652 is well suited for producing uridoms in accordance with the invention.

The elasticity-enhancing addition of paraffinic oil should preferably be in the range of 60 to 85 parts of paraffinic process oil per 100 parts of said copolymers, as a smaller amount of additive has proved not to produce the desired effect in respect of elasticity enhancement and reduced decontraction and unrolling force, whereas a larger amount of additive results in an unwarranted reduction of the strength properties of the uridom.

In addition, with a view to the injection moulding process forming part of the production method, a release agent is added, as it is prescribed per se for use of the said polymer materials in injection moulding. In connection with the production of uridoms which are to be stuck to the penis either, as shown in FIGS. 1 and 2 by means of an integral adhesive layer or by means of a separate adhesive strip, it has been found that the amount of additive release agent should be kept at a low level, wherefore the added release agent preferably is only 0.1~0.3 parts per 100 parts of polymer material. It has also been found that sufficiently good release properties can be achieved to ensure a stable production at the same time maintaining good adhesion properties of the applied pressure-sensitive adhesive.

It has been found that an optimum combination of the desired product properties in respect of good elesticity, moderate decontraction and unrolling force together with satisfactory wear/lifetime properties which allow storage for a considerable length of time can be achieved using a base material which is composed as follows:

| | |
|---|---|
| KRATON G 1650 - polymer | 60 parts PHR |
| KRATON G 1652 - polymer | 40 parts PHR |
| WITCO 260, a paraffinic process oil supplied by Witco Chemical Corporation | 75 parts PHR |
| PICCOPLASTIC d150, a thermoplastic hydrocarbon resin supplied by Hercules Inc., USA | 20 parts PHR |
| IRGANOX 1001, an anti-oxidant supplied by Ciba-Geigy | 1 part PHR |
| IRGANOX ps800, a stabilizer supplied by Ciba-Geigy | 0.5 parts PHR |
| ARMOSLIP e, a eurocamide release agent supplied by Akzo Chemie | 0.25 parts PHR |

The unit of quantity PHR indicates the ratio of each individual constituent of the base material per 100 parts polymer material (per hundred rubber).

Figure 4:
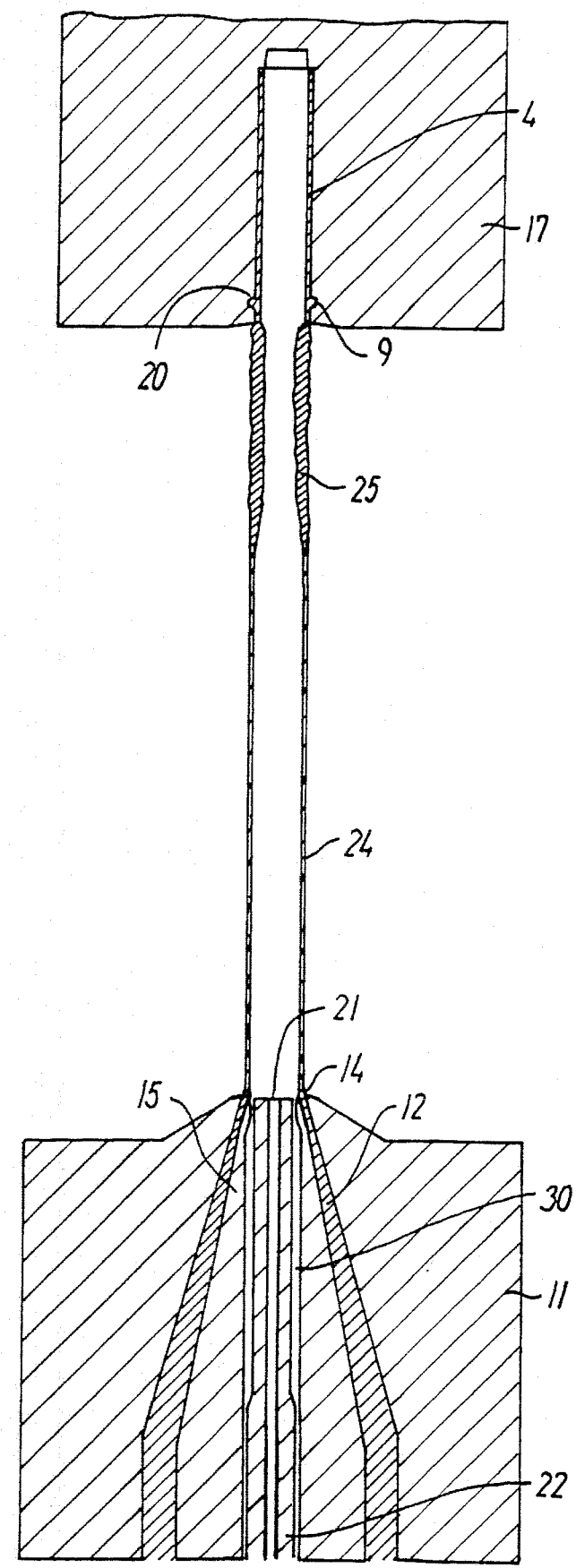
FIG. 4 illustrates the manufacture of the uridom through a pull extrusion process.
Figure 5:
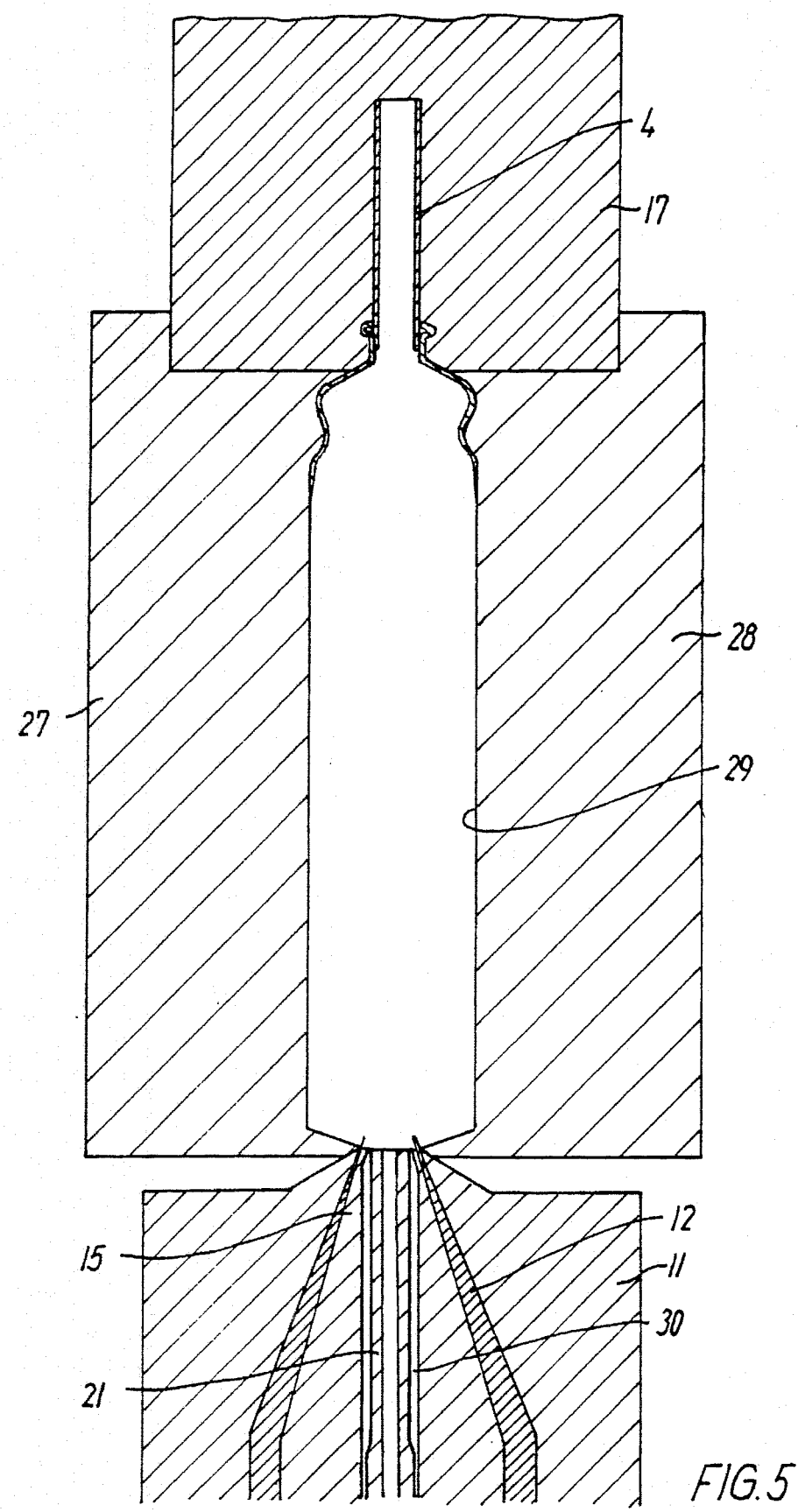
FIG. 5 illustrates the position of the uridom after the pull extrusion process.

In order to further illustrate the manufacturing of uridoms as shown in FIGS. 1 and 2, the parts of a thermoplastic processing apparatus, which in principle is known from European Patent Publications Nos. 0278399, 0278400, 0278401 and 0278402, necessary for understanding the invention are shown in FIGS. 3–5. Such an apparatus comprises, as shown in FIG. 3, a stationary first mould part 11 having a mainly cone-shell-shaped feeding duct 12 for feeding the abovementioned base material in a plastic state. The feeding duct 12 opens in a side wall 13 of the mould part 11 with an annular nozzle orifice 14, which can be opened and closed by means of an axially movable nozzle cone 15, the conical outer side of which together with the inner wall of conical cavity 16 in the mould part 11 opening at the nozzle orifice make up the feeding duct 12. For closing of the nozzle orifice 14 the nozzle cone 15 has on the major part of its length a smaller apex angle than the conical cavity 16.

Figure 6:
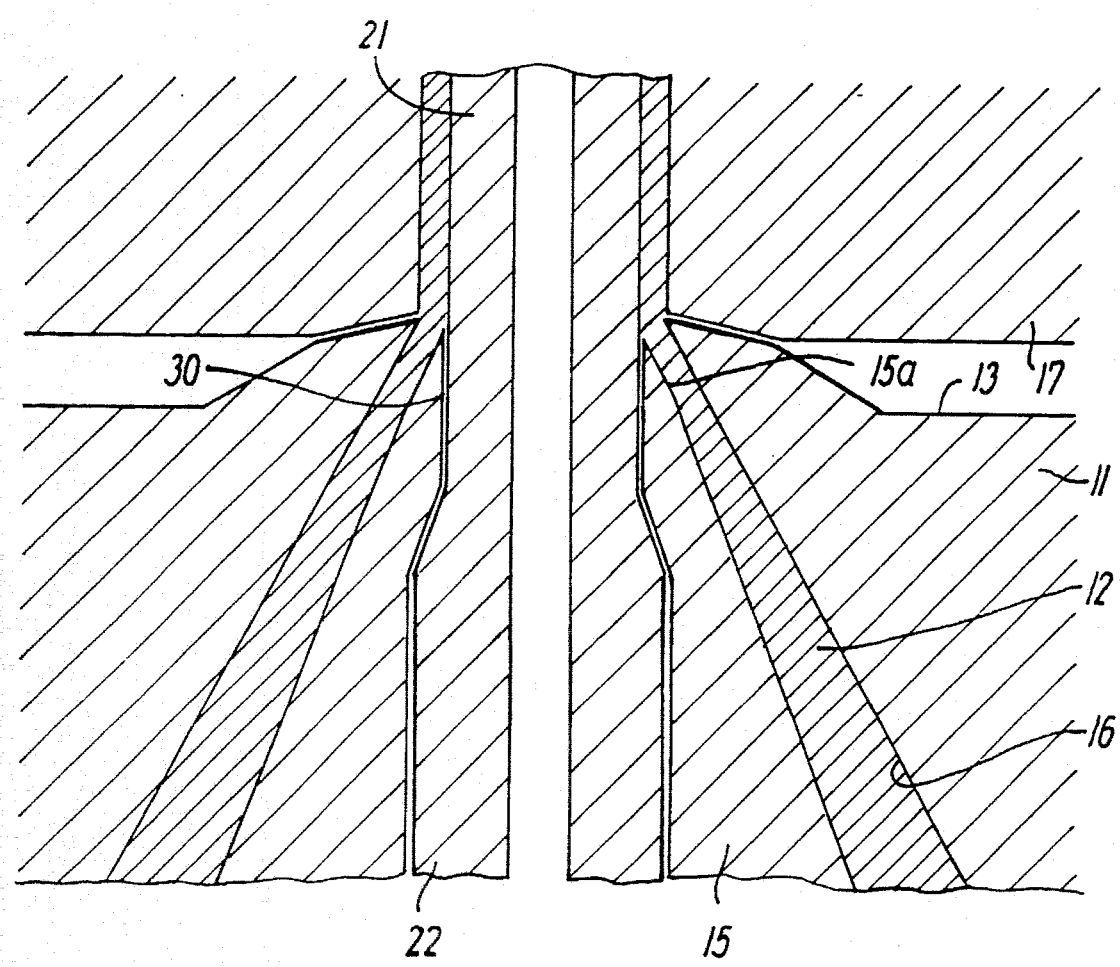
FIG. 6 illustrates a detail of the pull extrusion and blow moulding process.

However, the extreme portion 15a of the nozzle cone, positioned in the nozzle orifice as shown in the enlarged sectional view of FIG. 6 is homothetic to the wall of the conical cavity 16 around the nozzle orifice.

An injection moulding mould part 17 is arranged for movement towards and away from the side wall 13 of the stationary mould part 11 and comprises a tubular mould cavity 18, one end of which is open towards a side wall 19 for positioning against the nozzle orifice 14.

The tubular mould cavity has a diameter corresponding to the desired outer diameter of the drainage tube 4 of the uridom and an incision 20 for provision of the circular bead 9. As core element for provision of the clear of the drainage tube 4, a mandrel 21 is mounted in the nozzle cone 15 and connected to an axially movable piston rod 22, so that the mandrel 21 as shown in FIG. 3, during the injection moulding process can be pushed up into the mould cavity 18, which in its closed end has a depression with a reduced diameter to receive the end of the mandrel 21.

With the mandrel 21 in the position shown in FIG. 3 pushed into the mould cavity 18, the drainage tube 4 of the uridom is produced by injection moulding, the above-mentioned base material in a plastic state being fed through the feeding duct.

After cooling of the injection-moulded drainage tube the mandrel 21 is retracted into the nozzle cone 15 by means of the piston rod 22 to the position shown in FIG. 4, preparing for the next step of the thermoplastic processing which consists in a pull extrusion operation, during which the injection moulding mould part 17 and the injection-moulded drainage tube 4 retained therein by means of the bead 9 in the incision 20 are moved away from the first mould part 11. During the pull extrusion process and during continuous feeding of the base material through the duct 12, a hose-like member 24 is produced as shown in FIG. 4, and for achievement of the increased wall thickness in the end portion 3 in FIG. 2 of the uridom the speed at which the injection mould part moves away from mould part 11 is controlled in a way so that it moves relatively slowly at first to obtain the increased product thickness as shown at 25 in FIG. 4, and picks up speed during manufacturing of the remaining part of the hose-like member 24, which during the subsequent blow moulding operation forms the thin-walled body portion of the uridom.

In order to ensure sufficient material supply for manufacturing the end portion 3 in FIG. 2 during the extrusion process, the above-mentioned shape of the tip of the nozzle cone 15, having a conicity homothetic to the conicity of the cavity 16 around the nozzle orifice 14, so that on a short stretch a uniform width of the feeding duct 12 is obtained, has proved essential.

After the pull extrusion process the nozzle orifice 14 is closed by means of the nozzle cone 15, which assumes the position shown in FIG. 5. With the injection mould part 17 secured in the upper position, two mould wall parts 27 and 28 are introduced between mould parts 11 and 17 by a sideways movement to provide a mould cavity 29, having a contour corresponding to the body portion 1 of the uridom, and the extruded hose-like member is blown up in mould cavity 29 by injecting compressed air through the duct 30 provided in the mantel 21.

After a short cooling time the uridom can be removed from the mould, cut at the open end and be placed on a mandrel and an adhesive and adhesive rejecting layer be applied, after which the uridom is rolled up.

The invention is not limited to the examples given above, since as base material also other polystyrene-based block copolymers such as, e.g. SBS OR SIS polymers, to which the addition of paraffinic process oil will result in an enhanced elasticity, can be employed.

Furthermore, when applying the described method of manufacturing, the injection-moulded drainage tube can also be secured in the injection moulding mould part by means of a number of circular beads or other types of protrusions on the outer side of the drainage tube or, possibly, by providing the free end of the drainage tube with a protruding collar which is subsequently cut off.

As compared with the conventional manufacturing technology the combined injection moulding, pull extrusion and blow moulding gives a considerably increased freedom of choice in respect of the design the drainage tube and the adjacent end portion of the uridom.

Examples of this are shown in FIGS. 7–10.

Figure 7:
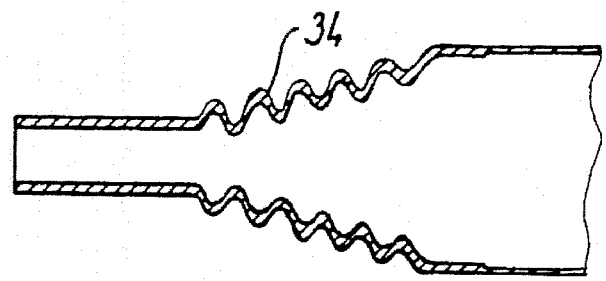
FIG. 7 shows a first alternative embodiment of the part of the uridom produced in the injection moulding process.

A high protection against kinking can thus be obtained as shown in FIG. 7 by designing at least a part 34 of the end portion of the uridom as a corrugated hull, which partly allows a significant angular displacement between the axial direction of the drainage tube and the uridom arranged on the penis, partly can absorb uridom tension and pressure loads. The hull portion 34, which has an increased wall thickness as compared with the body portion of the uridom is produced in the pull extrusion and blow moulding process through the above-mentioned control of the speed of the movable mould part, while using mould wall parts having a shape corresponding to the desired hull shape.

Figure 8:
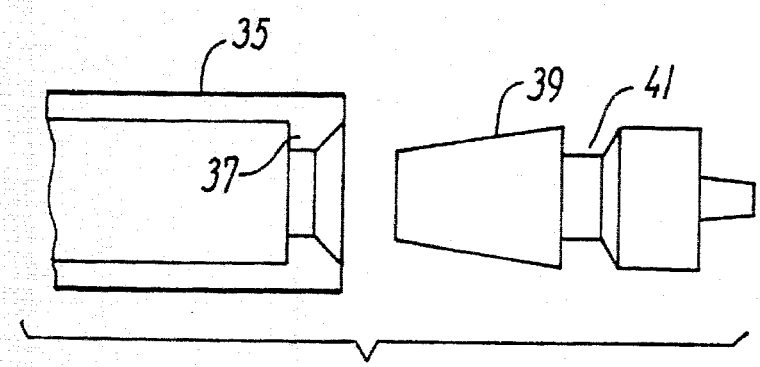
FIG. 8 shows a second alternative embodiment of the part of the uridom produced in the injection moulding process.
Figure 9:
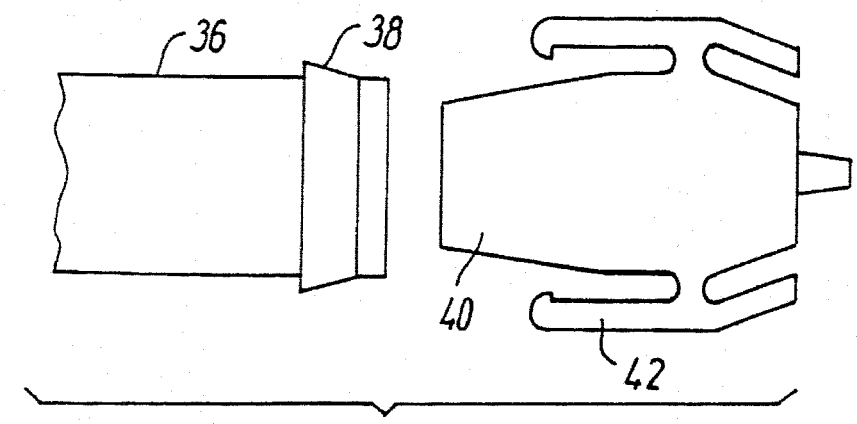
FIG. 9 shows a third alternative embodiment of the part of the uridom produced in the injection moulding process.

By providing the drainage tube 35 or 36 either with an inwards gripping collar 37 or an outwards gripping collar 38, as shown in FIGS. 8 and 9, for engagement with a corresponding gripping device on a tube connector 39, 40, either in the form of a circumferential groove 41 on the outer side of the connector 39 inserted in the drainage tube 35, or in the form of one or several external gripping claws 42, a more reliable joint between the drainage tube and the hose leading to the collection bag is ensured. In order to facilitate insertion and removal of the connector the extreme end of the drainage tube may furthermore be of a conical shape.

Figure 10:
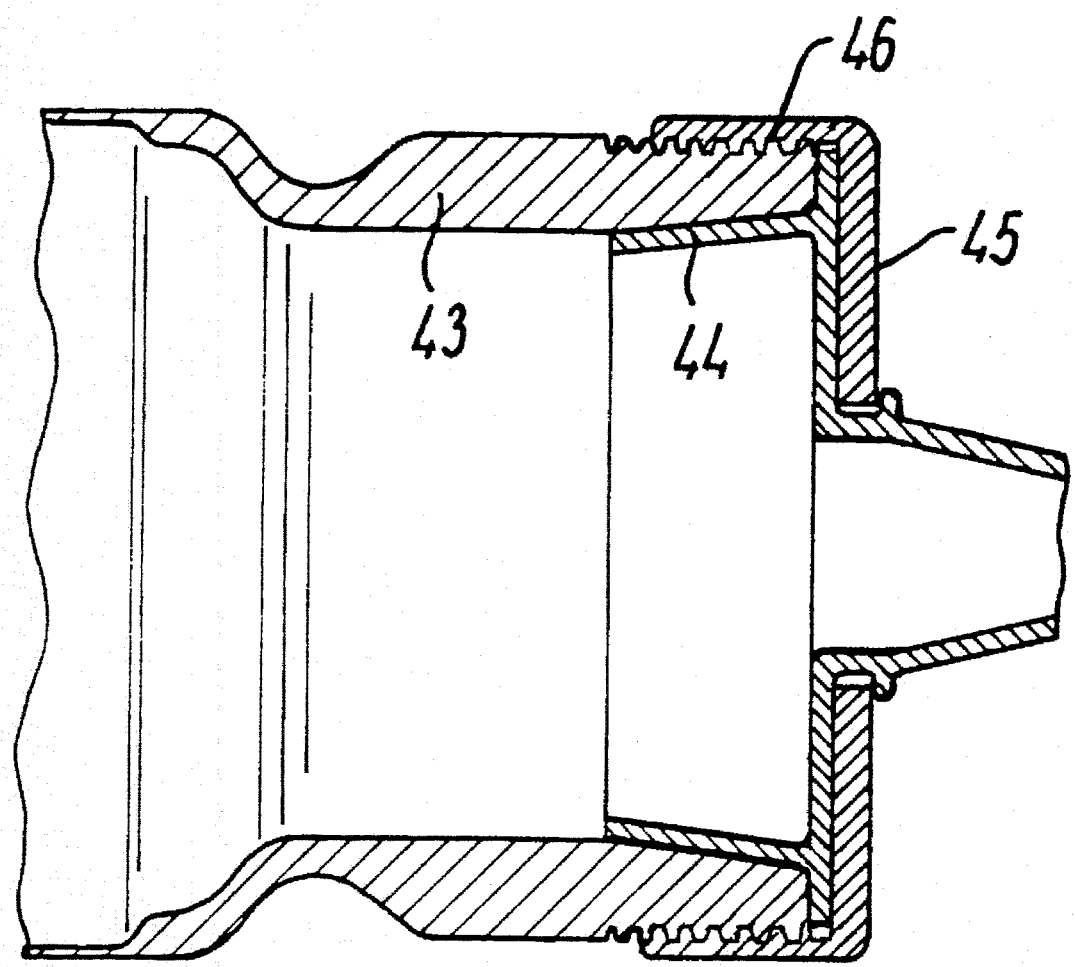
FIG. 10 shows a fourth alternative embodiment of the part of the uridom produced in the injection moulding process.

By designing the drainage portion 43 as shown in FIG. 10 with a short length and a comparatively large clear and with external engagement members, e.g. in the form of a thread 46 for tight but removable connection to a tube connector, comprising an internal lining collar 44 and an external tube union 45, a uridom is produced which allows urination by internal catheterization without removal of the uridom, the increased clear providing direct access for application of a catheter in the exposed urethra by removing the tube connector 44.

I claim:

1. A unitary uridom for use as an external catheter and a male unitary incontinence device consisting essentially of a single layer, unitary, tubular length of thermoplastically processed non-preprocessed thermoplastic elastomeric base material comprising an injection molded end portion, a combined pull extrusion and blow molded tubular portion and a combined pull extrusion and blow molded body portion, said end portion extending from a first end of said uridom and having a controlled wall thickness, said tubular portion connecting said end portion to said body portion, and said body portion being thin-walled and having a wall thickness which is less that a wall thickness of said end portion.

2. The uridom of claim 1, wherein said body portion has a constant width greater than a width of said end portion and said tubular portion increases in width from said end portion to said body portion.

3. The uridom of claim 1, wherein said tubular portion is constricted as compared to the body portion and is provided with either an inward or outward gripping collar for engagement with a corresponding gripping device on a tube connector extending toward said end portion.

4. The uridom of claim 1, wherein at least a part of said tubular portion is shaped as a corrugated hull having, in cross section, alternating ridges and grooves.

5. The uridom of claim 1, wherein said thin walled body portion includes an internal layer of pressure-sensitive adhesive and an adhesive-rejecting layer on the outside.

6. The uridom of claim 5, wherein said thermoplastic elastomeric base material comprises a polystyrene-based block polymer whose elasticity has been increased by the incorporation therein of 60 to 85 parts of paraffinic process oil per 100 parts of block polymer.

7. The uridom of claim 6, wherein said tubular portion is constricted as compared to the body portion and is provided with either an inward or outward gripping collar for engagement with a corresponding gripping device on a tube connector extending toward said end portion.

8. A unitary uridom for use as an external catheter in a male urinary incontinence device, said uridom being manufactured by thermoplastic processing of a non-preprocessed thermoplastic elastomeric base material, a tubular portion at a first end of said uridom having a controlled wall thickness produced by injection moulding in a tool and a substantially cylindrical thin-walled body portion having an end portion communicating with said tubular portion, said end and body portions being produced by a subsequent controlled pull extrusion and blow moulding process, during which said tubular portion is secured and retained in said tool, said thin-walled body portion having a lesser wall thickness than a wall thickness of said end portion, wherein said end portion including one or more zones in a longitudinal direction of said body portion, said zones having an increased wall thickness as compared with the remainder of said body portion said zone or zones adjacent said tubular portion, the wall thickness of said zone or zones being greater than the controlled wall thickness of said tubular portion.

9. The uridom of claim 8 wherein said end portion is provided with a circumferential constriction to receive said body portion in rolled-up condition and to provide a bulbous anti-kinking chamber.

10. The uridom of claim 8, wherein at least a part of said end portion of the uridom is shaped as a corrugated hull having, in cross section, alternating ridges and grooves.

11. The uridom of claim 8, wherein said tubular portion is constricted as compared to the body portion and is provided with either an inwards or outwards gripping collar for engagement with a corresponding gripping device on a tube connector extending towards said tubular portion.

12. The uridom of claim 8, wherein said thin-walled body portion includes an internal layer of a pressure-sensitive adhesive and an adhesive-rejecting layer on the outside.

13. A kit having a unitary uridom and a lining collar, wherein the unitary uridom is for use as an external catheter in a male urinary incontinence device, said uridom being manufactured by thermoplastic processing of a non-preprocessed thermoplastic elastomeric base material, a tubular portion at a first end of said uridom having a controlled wall thickness produced by injection moulding in a tool and a substantially cylindrical thin-walled body portion having an end portion communicating with said tubular portion, said end and body portions being produced by a subsequent controlled pull extrusion and blow moulding process, during which said tubular portion is secured and retained in said tool, said thin-walled body portion having a lesser wall thickness than a wall thickness of said end portion, said tubular portion has a short length and a comparably large orifice, said tubular portion including external threads for tight but removable connection to a tube union, and the lining collar being insertable in the orifice of said tubular portion.

* * * * *